United States Patent [19]

Ebersberger et al.

[11] Patent Number: 5,313,510
[45] Date of Patent: May 17, 1994

[54] X-RAY TUBE FOR COMPUTER TOMOGRAPHY

[75] Inventors: Johannes Ebersberger, Erlangen; Heinrich Stoehr, Adelsdorf, both of Fed. Rep. of Germany

[73] Assignee: Siemens Aktiengesellschaft, Munich, Fed. Rep. of Germany

[21] Appl. No.: 913,912

[22] Filed: Jul. 17, 1992

[30] Foreign Application Priority Data

Jul. 22, 1991 [DE] Fed. Rep. of Germany ....... 4124294

[51] Int. Cl.⁵ .............................................. H01J 35/30
[52] U.S. Cl. ...................................... 378/12; 378/137
[58] Field of Search ............................ 378/11, 12, 137

[56] References Cited

U.S. PATENT DOCUMENTS

| | | | |
|---|---|---|---|
| 4,637,040 | 1/1987 | Sohval | 378/19 |
| 4,748,650 | 5/1988 | Ammann . | |
| 4,912,739 | 3/1990 | Weiss . | |

FOREIGN PATENT DOCUMENTS

| | | |
|---|---|---|
| 2902308 | 8/1979 | Fed. Rep. of Germany . |
| 3113368 | 10/1982 | Fed. Rep. of Germany . |
| 1469932 | 4/1977 | United Kingdom . |
| 1604431 | 12/1981 | United Kingdom . |

Primary Examiner—Craig E. Church
Attorney, Agent, or Firm—Hill, Steadman & Simpson

[57] ABSTRACT

An x-ray tube for computer tomography (CT) has a cathode for generating an electron beam, a rotating anode having an incident area onto which the electron beam is incident in a focal spot, and a deflection system for deflecting the electron beam, dependent on an electrical deflection signal, in a deflection direction intersecting the circumferential direction of the rotating anode, such that the focal spot periodically moves from an initial position into a final position once during once per scanning position.

68 Claims, 15 Drawing Sheets

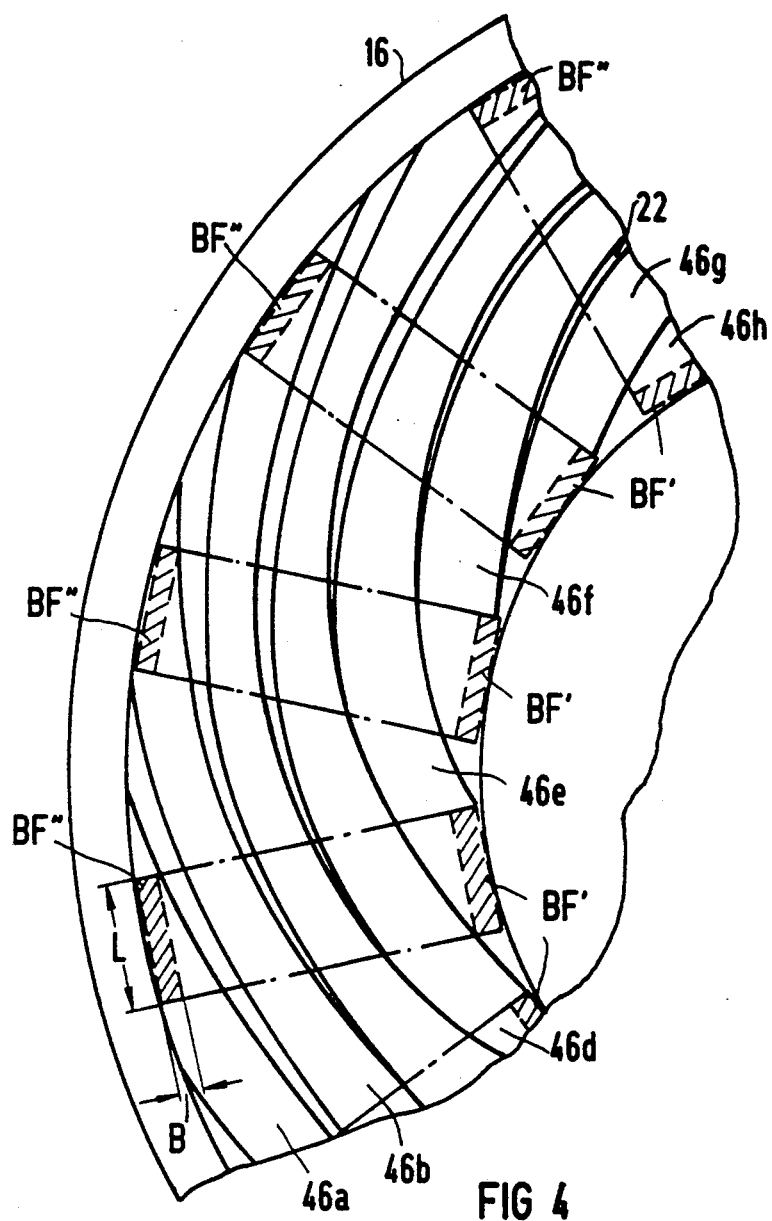

X-RAY TUBE FOR COMPUTER TOMOGRAPHY

BACKGROUND OF THE INVENTION

1. Field of the Invention

The present invention is directed to an x-ray tube, particularly for computer tomography (CT), having a cathode for generating an electron beam, a rotating anode having an incident area onto which the electron beam is incident in a focal spot, and deflection means for deflecting the electron beam dependent on an electrical deflection signal such that the focal spot periodically moves from a starting into a final position, preferably with a constant period.

2. Description of the Prior Art

X-ray tubes of the above type are employed for computer tomography since an improvement in the image quality can be achieved as a consequence of the periodic movement of the focal spot, by doubling the data available for calculating an image of a body slice. The deflection ensues such that the focal spot moves essentially in the circumferential direction of the rotating anode or tangentially relative to that circumferential direction.

Since the time required for generating an image of a body slice is extremely short as a consequence of progress achieved in the field of computer tomography and, moreover, the radiation dose administered to a patient in the preparation of an image is extremely low, the desire has recently arisen to be able to produce a plurality of images in immediate succession of the same body slice, or of body slices lying in extremely close proximity in order to thus improve the conditions for a reliable diagnosis. This, however, is only possible to a limited scope since there is a risk of overloading the x-ray tube employed.

SUMMARY OF THE INVENTION

It is an object of the present invention is to provide an x-ray tube of the type described above having a higher thermal loadability.

This object is achieved in accordance with the principles of the present invention in an x-ray tube, particularly for computer tomography, having a cathode for generating an electron beam, a rotating anode having an incident area onto which the electron beam is incident in a focal spot, and deflection means for deflecting the electron beam. The deflection means periodically deflects the electron beam in a deflection direction intersecting the circumferential direction of the rotating anode dependent on an electrical deflection signal such that the focal spot moves from a starting position into a final position. By contrast to the prior art, wherein the area of the portion of the incident are swept by the focal spot remains essentially unaltered as a consequence of the motion of the focal spot in the circumferential direction, an enlargement of the area of the region of the incident area swept by the focal spot is achieved in the invention as a consequence of moving the focal spot in a direction intersecting the circumferential direction. This enlargement is achieved both for given dimensions of the rotating anode and of the focal spot, and for a given speed. Since the thermal loadability of the focal spot increases with the root of that factor by which the area of the region of the incident area swept by the focal spot increases, an improved loadability of the x-ray tube of the invention is achieved. With other factors being constant, the loadability increases as the deflection frequency, i.e. the frequency of the deflection signal becomes higher, as the distance the focal spot traverses upon movement from a starting position into the final position becomes longer, and as the distance between the starting position and the final position measured transversely relative to the circumferential direction increases.

As used herein "focal spot" is the effective focus area from which the x-radiation proceeds. The region wherein the electron beam impinges the incident area can be significantly smaller than the focal spot. The focal spot may be generated in the manner disclosed in European Patent Application 0 150 364 wherein the electron beam, in addition to executing the inventive deflection motion intersecting the circumferential direction of the rotating anode, executes a second deflection motion that is of such a nature that the focal spot is scanned by the electron beam. The second deflection motion has less of an amplitude and a significantly higher frequency than the inventive deflection motion which intersects the circumferential direction. For example, the second deflection motion can be realized with a corresponding, second electrical deflection signal that is superimposed on the electrical deflection signal that effects the deflection motion that intersects the circumferential direction of the rotating anode.

In an embodiment of the invention the deflection means deflect the electron beam so that the distance between the final position and the starting position measured transversely relative to the circumferential direction is at least equal to four times the extent of the focal spot transversely relative to the circumferential direction. An approximate doubling of the thermal loadability of the focal spot can be theoretically realized in this way. The deflection means preferably deflects the electron beam so that the distance from the final position to the starting position measured transversely relative to the circumferential direction is at least equal to twenty-five times the extent of the focal spot transversely relative to the circumferential direction. Compared to a traditional x-ray tube, five times the thermal loadability of the focal spot is theoretically achieved in this case, which can still be realized within the traditional dimensions of focal spot and anode. A maximum increase in the thermal loadability of the focal spot can be achieved for given conditions if the deflection means deflect the electron beam that the distance between the final position and the starting position measured transversely relative to the circumferential direction at least essentially corresponds to the extent of the incident area transversely relative to the circumferential direction.

In a further embodiment of the invention, the rotatory frequency of the rotating anode is not a whole multiple of the deflection frequency with which the deflection means deflect the electron beam, and the deflection frequency is not a whole multiple of the rotatory frequency. This achieves an interleaving of those regions of the incident area respectively swept by the focal spot on its path from the starting position into the final position in successive revolutions of the rotating anode. The advantage thereof is that a region swept by the focal spot on its path from the initial position into the final position is only swept again on the path of the focal spot from its initial position into its final position after several revolutions of the rotating anode. The deflection frequency can be either greater or lesser than the rotatory frequency; the region of the incident area swept by the focal spot on its path from the initial position into the final position covering more than 360° in the former instance and less than 360° in the latter instance. Particularly when the deflection frequency is extremely large or extremely small in comparison to the rotatory frequency, however, it can also be expedient for the rotatory frequency to be a whole multiple of the deflection frequency, or for the deflection frequency to be a whole multiple of the rotatory frequency.

In order to assure that the focal spot sweeps the incident area in the desired way, it is provided in an embodiment of the invention that the deflection frequency and the rotatory frequency are fixedly coupled to one another. The two frequencies thus reside in a constant ratio relative to one another, so that it is guaranteed that the focal spot sweeps exactly the provided regions of the incident area. Fluctuations in the rotatory frequency must be avoided (as is known) since problems in the data compilation during the CT measuring process could otherwise arise.

It is provided in a preferred embodiment of the invention that the deflection frequency and the signal shape of the deflection signal are selected such dependent on the rotatory frequency, direction and course (for example, straight-line or curved), on the dimensions and the geometrical shape of the incident area, on the distance of the final position from the starting position measured transversely relative to the circumferential direction as well as on the extent of the focal spot in circumferential direction and transversely relative thereto so that the regions of the incident area respectively swept by the focal spot on its path from the initial position to the final position are arranged as closely as possible to one another without overlapping one another. The available incident area is thereby optimally utilized and the maximally possible thermal loadability of the focal spot is achieved for the said data when the regions of the incident area respectively swept by the focal spot on its path from the initial position to the final position are immediately adjacent to one another.

In a further version of the invention the focal spot moves on a straight line from the starting position into the final position. A technologically simple fashioning of the deflection means thereby becomes possible. Moreover, the CT measuring process takes on a simple aspect. Fundamentally, however, it is also possible to provide a different motion, for example a curved motion even though this can complicate the CT measuring process.

In another preferred embodiment of the invention the deflection signal has such a signal shape so that the focal spot moves discontinuously from the starting position into the final position with at least one intermediate position. In this case, the focal spot on the incident area sweeps a circularly curved region while it dwells in each of the initial position and final position as well as in each of the intermediate positions. If the deflection signal has such a signal shape that the focal spot remains in the initial position, in every intermediate position and in the final position for the respective duration of an entire revolution of the rotating anode, an especially good utilization of the incident area is achieved since the focal spot sweeps an annular region of the incident area in each of the said positions. Since the deflection frequency is then equal to the quotient of the rotatory frequency and the number of intermediate positions incremented by two, the rotatory frequency is a whole multiple of the sampling frequency in the case set forth.

In another preferred embodiment of the invention the deflection signal has such a signal shape that the focal spot moves from the starting position into the final position in a continuous motion, preferably with constant speed with reference to the housing of the x-ray tube. In this case, the focal spot moving from the initial position into the final position sweeps respective regions of the incident area that, in the broadest sense, have a helical shape or are sections of helices.

In another embodiment of the invention the generation of x-radiation is suppressed in the duration between each attainment of the final position and the subsequent renewed beginning of the motion of the focal spot again proceeding from the initial position. Overlapping of the regions of the incident area swept during the motion of the focal spot from the initial position into the final position and those regions in the incident area that are swept during the motion of the focal spot from the final position back into the initial position are thereby reliably suppressed. If such overlapping is not undesired, however, it can also be provided that the deflection of the electron beam ensues in oscillatory fashion, such that the focal spot moves between the initial position and the final position in a back and forth motion.

In another version of the invention the deflection signal has such a signal shape that the time during which the focal spot moves from the initial position into the final position is multiply greater, preferably at least ten times greater, than the time between the attainment of the final position and the renewed beginning of the motion of the focal spot proceeding from the initial position. This offers the advantage that a suppression of the generation of x-radiation during the times respectively elapsing between the attainment of the final position and the renewed beginning of the motion of the focal spot proceeding from the initial position is not absolutely necessary.

In another preferred embodiment of the invention, the mass and the surface of the rotating anode are selected (taking into account the other parameters that are critical for the heat exchange by radiation between the rotating anode and the vacuum housing which surrounds it) so that a stationary pre-temperature of the rotating anode is established, which is at least essentially equal to the maximally allowable pre-temperature of a corresponding, traditional x-ray tube under continuous operation with maximum power. The term "pre-temperature" means that temperature which a point of the rotating anode swept by the focal spot has immediately before entry into the electron beam. As a consequence of the limited thermal loadability of the focal spot, it is not possible in traditional x-ray tubes to operate the rotating anode at such a temperature that the quantity of heat supplied to the rotating anode per time unit during normal operation is simultaneously in turn eliminated by radiation, this being a prerequisite for a stationary pre-temperature. The rotating anodes of traditional x-ray tubes are therefore dimensioned as heat stores having a high mass, with the consequence that the operation of the x-ray tube must be interrupted when the heat capacity of the rotating anode is exhausted, this being extremely undesirable given practical employment of the x-ray tube in medicine. As a consequence of the improved thermal loadability of the focal spot of the x-ray tube of the invention, however, it is possible, given suitable dimensioning of the rotating anode, to realize a stationary pre-temperature of the rotating anode that preferably corresponds to the maximally allowable pre-temperature in corresponding, traditional x-ray tubes even given maximum power. Since the temperature of the rotating anode (to the fourth power) is a factor in the heat quantity that can be eliminated by radiation per time unit, it is clear that even relatively slight elevations in the temperature of the rotating anode considerably improve its thermal radiation capability. Apart from the fact that interruptions in the operation of the x-ray tube because of impending thermal overload are thus avoided, the advantage of a decreased mass of the rotating anode is also achieved. The latter has a beneficial effect on the loading, and thus on the useful life, of the bearing of the rotating anode and also shortens the running time necessary to bring the rotating anode up to speed.

Although it is possible to realize x-ray tubes in accordance with the principles of the present invention having a planar, annular incident area, in a preferred version of the invention the incident area is shaped as a cylindrical envelope. This permits substantially the entire surface of the incident area to be swept by the focal spot without difficulty.

DESCRIPTION OF THE DRAWINGS

FIG. 4 is an enlarged view of a portion of the incident area of FIG. 3.

FIGS. 5a and 5b through 9 are highly schematic views of the incident area of the rotating anode of the x-ray tube according to FIG. 1 for different deflection signals $I_A$ and different deflection directions.

DESCRIPTION OF THE PREFERRED EMBODIMENTS

Figure 1:
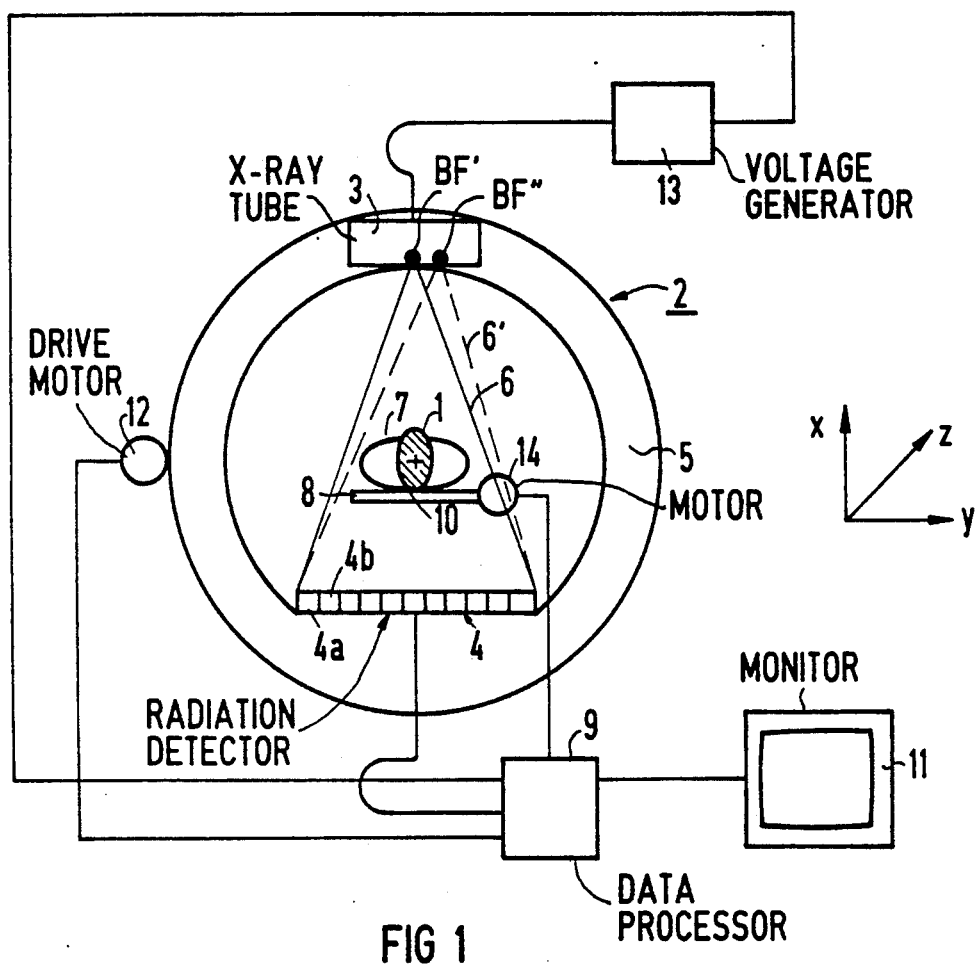
FIG. 1 is a schematic view of a computer tomography apparatus containing an x-ray tube constructed in accordance with the principles of the present invention.

The computer tomography apparatus 2 shown in FIG. 1 has an x-ray tube 3 which, together with a radiation receiver 4, forms an actinometer. The radiation receiver 4 is formed by a row of individual detectors 4a, 4b, etc. The x-ray tube 3 is fixedly connected to the radiation receiver 4 via a rotating frame 5 and emits a fan-shaped x-ray beam 6 that penetrates a slice of a body part to be examined by means of the generation of an image thereof, for example the head of a patient 1. The patient 1 lies on a patient support 8. The expanse of the x-ray beam 6 perpendicular to the plane of the drawing corresponds to the thickness of the slice 7. The number of individual detectors 4a, 4b, etc. in the radiation receiver 4 is selected according to the desired image resolution. Each individual detector 4a, 4b, etc, generates an electrical signal that corresponds to the intensity of the respectively received x-radiation.

The individual detectors 4a, 4b, etc. of the radiation receiver 4 are connected to an electronic data processor 9 that calculates the x-ray attenuation values of the individual volume elements of the slice 7 from the output signals of the individual detectors 4a, 4b, etc. during the rotation of the actinometer around a rotational axis 10 that proceeds parallel to the longitudinal direction of the patient support 8 and perpendicular to the plane of the x-ray beam 6. The coordinates of the volume elements are recited with reference to a device-fixed, rectangular coordinate system having the axes x, y, z. On the basis of the calculated x-ray attenuation values of the individual volume elements of a scanned slice 7, the electronic data processor 9 calculates a tomogram of this slice that can be displayed on a monitor 11, whereby a specific chromatic value or gray scale value in the illustration of the tomogram corresponds to a specific x-ray attenuation value.

The scanning of a slice 7 usually ensues given a complete rotation of the actinometer around the axis 10, with a set of output signals at the radiation receiver 4 being generated for a complete scan event with, for example, scanning positions offset relative to one another by only one angular degree. Given, for example, 512 individual detectors in the radiation receiver 4, 360×512 output signals are thus generated in conventional computer tomography apparatusses per scan event. These form the basis for the calculation of the x-ray attenuation values of the volume elements of the scanned slice.

In the illustrated exemplary embodiment, only a few of the individual detectors have been shown, for clarity.

In more recent computer tomography apparatusses as the one shown in FIG. 1, however, the focal spot of the x-ray tube 3 from which the fan-shaped x-ray beam emanates is displaceable from an initial position BF' to a final position BF" for ever scanning position of the scan event. The slice to be imaged is thus additionally penetrated by the fan-shaped x-ray beam 6' in the way indicated with broken lines in FIG. 1, so that 2×360×512 output signals of the radiation receiver 4 are generated per scan event. The electronic data processor 9 uses these for generating an single image. It has been shown that the image quality of images produced in this way is improved when compared to traditionally produced images. Practice has also shown that an especially good suppression of artifacts is possible if the x-ray tube 3 is not pulsed (i.e., such that the x-ray generation ensues only in the initial point and in the final point of the described displacement of the focal spot BF) but instead ensues continuously, as a consequence of the "smearing" that then arises. It is to be understood, that if the actinometer rotates continously, as is normally the case, the sampling of the output signals does not ensue at exactly the same angular position of the actinometer for corresponding positions BF' and BF" of the focal spot. As the angular difference is only small, however, the angular positions in which the sampling of the output signals corresponding the positions BF' and BF" of the focal spot ensues are herein referred to as one scanning position. The x-ray generation need not necessarily be interrupted for the motion of the focal spot from the final position back into the initial position (this motion preferably ensues during a significantly shorter time span than the motion from the initial position into the final position). This, however, will normally be the case.

The rotation of the rotating frame 5 is produced with a motor 12 that is actuated in the required way by the electronic data processor 9. To be able to image different slices, the patient support is adjustable in the z-direction with a motor 14 that is likewise controlled by the electronic data processor 9. The x-ray tube 3 is supplied with the necessary voltages by a voltage generator 13, which is likewise controlled by the electronic data processor 9 in the required way. The generator 13 also supplies a deflection signal that serves the purpose of displacing the focal spot of the x-ray tube 3 in the aforementioned manner and also supplies a control signal that serves the purpose of suppressing the generation of x-radiation, as needed.

Figure 2:
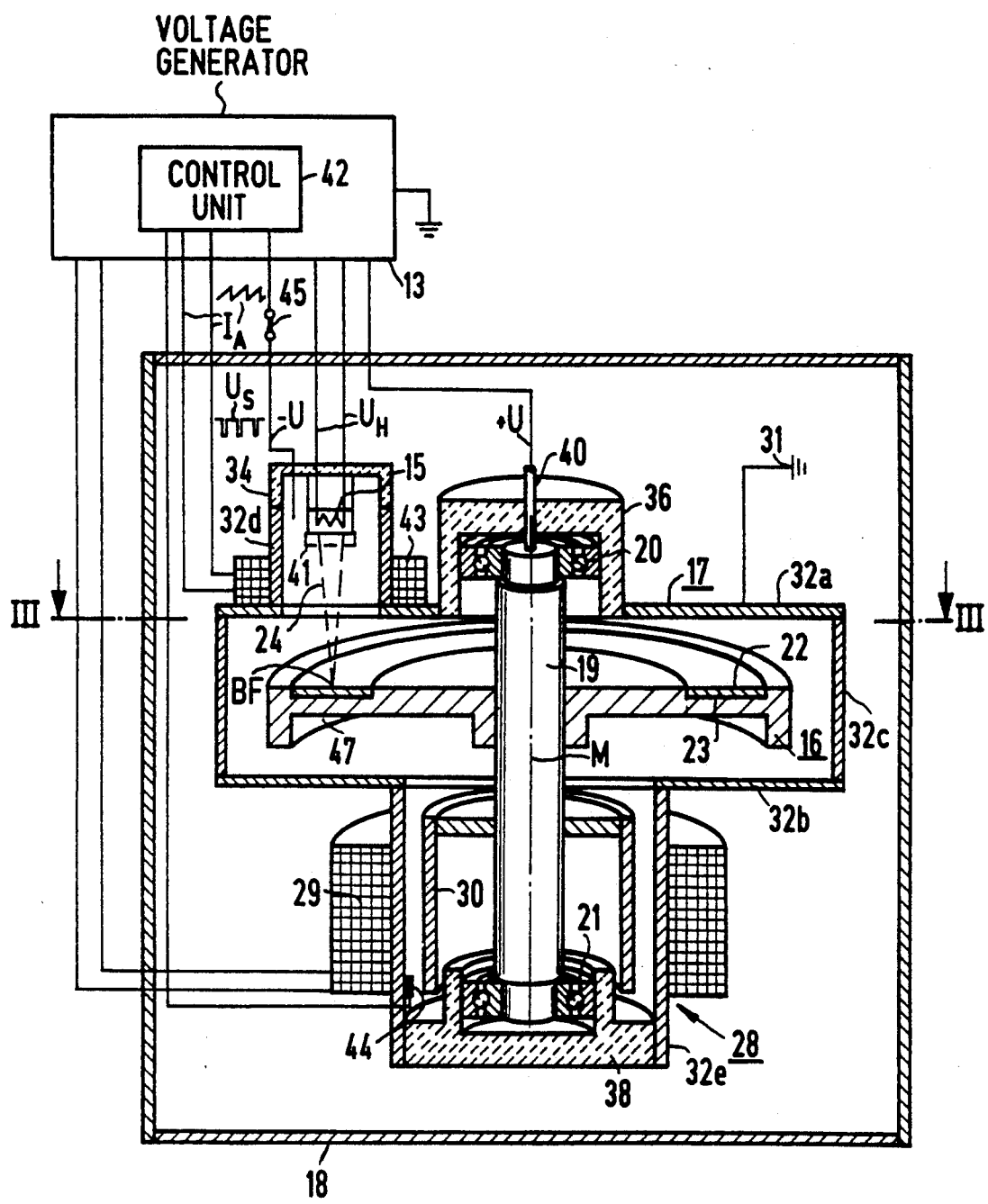
FIG. 2 is a schematic longitudinal sectional view of an x-ray tube constructed in accordance with the principles of the present invention.
Figure 3:
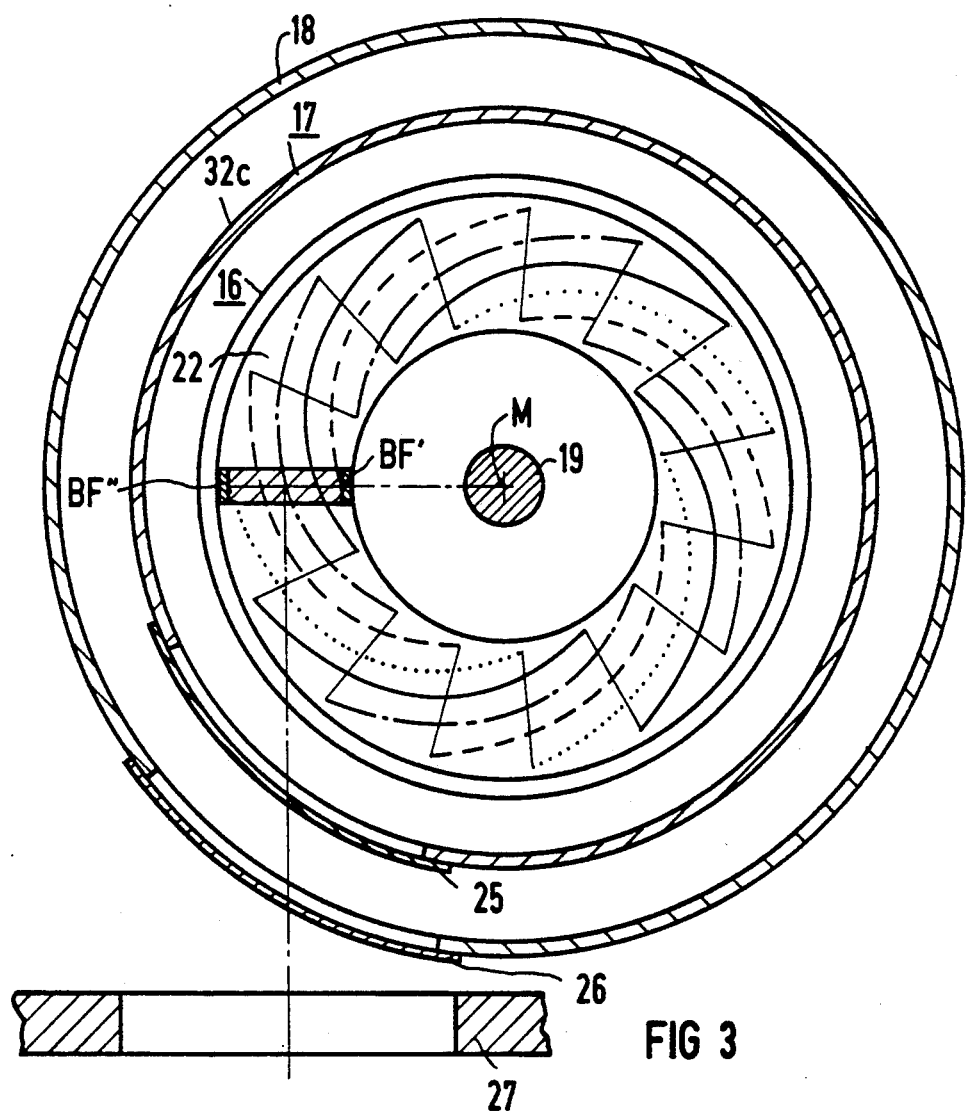
FIG. 3 is a sectional view taken along line III—III in FIG. 2.

FIGS. 2 and 3 show the x-ray tube 3 in greater detail. The x-ray tube 3 has a stationary cathode 15 and a rotating anode, generally referenced 16, which are arranged in an evacuated housing 17 that is in turn accepted in a protective housing 18 filled with an electrically insulating, liquid coolant, for example insulating oil. The rotating anode 16 is rotatably seated in the housing 17 or a shaft 19 and two rolling bearings 20, 21. The rotating anode 16 is dynamically balanced vis-a-vis the center axis M of the shaft 19 and has a planar, annular incident area 22 for the electron beam 24 emanating from the cathode 15. The incident area 22 is formed by a layer 23 of a tungsten-rhenium alloy. The useful ray beam emanating from the focal spot BF, i.e. from the point of incidence of the electron beam 24 on the incident area 22, (only the central ray Z of this useful ray beam being shown for a middle focal spot position in FIG. 3) emerges through radiation exit windows 25 and 26 arranged in registry and provided in the housing 17 and in the protective housing 18. The beam is then incident on a slot-shaped diaphragm 27 that shapes the fan-shaped x-ray beam 6 (see FIG. 1) required for the computer tomography.

The center axis M of the shaft 19 is inclined with respect to the plane of the drawing of FIG. 2, and the diaphragm 27 is arranged such that the central ray Z of the fan-shaped x-ray beam proceeds in a plane residing at a right angle relative to the plane of the drawing of FIG. 2. Since the focal spot BF is line-shaped, an increased thermal loadability of the focal spot BF is achieved by these measures in a known way. Theoretically, it would possible to employ a rotating anode having a conical frustum-shaped incident area, in which case a slope of the center axis of the rotating anode would then not be required. A conical frustum-shaped incident area, however, would result in the focal spot, when deflected in a way yet to be set forth, spatially twisting during the deflection and this would be disadvantageous for the image quality. For simplicity, the incline of the center axis M of the shaft 19 is not shown in FIG. 3.

An electric motor generally referenced 28 is provided for driving the rotating anode 16, this electric motor 28 being a squirrel-cage induction motor and having a stator 29 put in place on the housing 17 and a rotor 30 situated inside the housing 17 and torsionally connected to the shaft 19.

The vacuum-tight housing 17, which is at ground potential 31, is formed by two approximately plate-shaped housing parts 32a and 32b connected to a tubular housing part 32c, and a shaft-shaped housing part 32d that is connected to the housing part 32a. The housing parts 32a through 32d are preferably composed of metallic material. The cathode 15 is attached to the shaft-shaped housing part 32d with an insulator 34 that is connected to the housing part 32d. The housing part 32a has a central bore into which an insulator 36 that accepts the outer ring of the rolling bearing 20, is introduced with the required slope. The housing part 32b also has a bore into which a further tubular housing part 32e is introduced with the required slope, this housing part 32e accepting the rotor 30 in its interior and the stator 29 being put in place on the outer surface thereof. An insulator 38, that accepts the outer ring of the rolling bearing 21, is introduced into the free end of the housing part 18e. The feed of the positive high-voltage $+U$ for the rotating anode 16 ensues with a contact 40 pressing resiliently against the shaft 19 in a known way (not shown in detail). This contact 40 is accepted vacuum-tight in the insulator 36.

As may be seen from the schematic illustration of FIG. 2, the negative high-voltage $-U$ is at the one terminal of the cathode 15. The filament voltage $U_H$ is between the two terminals of the cathode 1. The lines leading to the cathode 15, the contact 40, to the housing 17 and to the stator 29 are in communication with the voltage generator 13 situated outside the protective housing 18. This generator 13 is fashioned in a standard way and supplies the voltages required for the operation of the x-ray tube 3.

The cathode 15 has a control grid 41 connected to a control stage 42 that is a component of the generator 13 and which, as needed, supplies the control grid 41 with a control voltage $U_S$ for placing the control grid 41 at such a potential during times wherein the generation of the x-rays should be suppressed, so that the electron beam 24 is interrupted by the control grid 41 and thus does not proceed to the incident area 22.

The housing part 32d is surrounded by a deflection coil 43 that is likewise connected to the control stage 42 and is charged by the latter with a deflection signal $I_A$ with which the electron beam 24 can be deflected in the plane of the drawing of FIG. 2, so that the focal spot BF can be shifted between an initial position BF' and a final position BF' on a straight-line, radial path (see FIG. 3) whose extension intersects the middle axis M of the rotating anode 16. The deflection signal $I_A$ is a periodic signal having a constant period whose frequency (the deflection frequency) is fixedly coupled to the rotatory frequency of the rotating anode 16. A sensor 44 is provided for this purpose, which generates a signal corresponding to the rotatory frequency (speed) of the rotating anode 16, which is supplied to the control stage 42 for synchronizing the deflection frequency with the rotatory frequency. For example, the sensor 44 can be an optoelectronic sensor that senses a mark applied to the stator 39. Since it is critical for the CT measuring process that the deflection frequency does not fluctuate, the signal of the sensor 44 can also be simultaneously employed to stabilize the rotatory frequency of the rotating anode 16, and thus the deflection frequency that is coupled thereto. This can occur in a known way, for example by comparing the signal of the sensor 44 to a reference signal and the rotatory frequency of the rotating anode 16 being correspondingly corrected in the event of deviations.

As indicted in FIG. 2, the deflection signal $I_A$ is preferably an approximately sawtooth-shaped signal, whereby the movement of the focal spot BF from its initial position BF' into its final position BF" ensues during the slightly rising, linear edge of the sawtooth-shaped deflection signal $I_A$ with a constant deflection speed with reference to the housing 17. The control voltage $U_S$ is an asymmetrical square-wave signal that assumes a voltage value for the duration of the steeply dropping edge of the sawtooth-shaped deflection signal $I_A$ that is more negative than the cathode potential. When the switch 45 is opened, consequently, the focal spot BF moves back from its final position BF" into its initial position BF' during the steeply dropping edge of the sawtooth-shaped deflection signal $I_A$. When, by contrast, the switch 45 is closed, the motion of the focal spot BF from its initial position BF' into its final position BF" ensues only during each gradually rising edge of the sawtooth-shaped deflection signal $I_A$.

In the present exemplary embodiment (see FIG. 3), the deflection frequency, i.e. the frequency of the deflection signal $I_A$, is higher than the rotatory frequency of the rotating anode 16 (such as the rotatory frequency amounting to 4/15 of the deflection frequency0, so that the rotary frequently is not a whole multiple of the deflection frequency, and the deflection frequency is not a whole multiple of the rotatory frequency. On the contrary, the deflection frequency-taking into consideration the radial direction and the straight-line course of the deflection motion, the rotatory frequency of the rotating anode 16, the outside diameter of the incident area 22, the extent of the focal spot BF in circumferential direction of the rotating anode and transversely thereto, as well as taking into consideration the distance of the focal spot from the initial position BF' to the final position BF" traversed transversely relative to the circumferential direction-is selected such that the regions of the incident area 22 respectively swept by the focal spot BF on its path from the initial position BF' to the final position BF" lie optimally close to one another without overlapping one another. As a consequence of the rigid coupling of the deflection frequency with the rotatory frequency, the focal spot BF thereby sweeps a path section in the shape of a section of a helix on its path from the initial position BF' into the final position BF". As a consequence of the extremely steeply drooping edge of the deflection signal $I_A$, the final position BF" of a preceding motion and the initial position BF' of the immediately following motion respectively lie approximately on the same radius. These conditions are shown in FIG. 3 for four revolutions of the rotating anode 16 (or for 15 periods of the deflection signal $I_A$), whereby the path described up to that time is then again swept. Only the path that the center of the focal spot describes on the incident area 22 of the rotating anode 16 is shown. The path is shown with a different line format for each of the revolutions. The parts of the path situated between the final positions BF" and the initial positions BF' are shown with thin lines since these parts of the path are in fact only swept when the switch 45 is opened. As may be seen from FIG. 3, the deflection motion of the focal spot BF-as indicated with shading-extends essentially over the entire width of the incident area 22.

FIG. 4 shows the actual conditions for a portion of the incident area 22. It can be seen that the path sections 46a through 46h respectively swept by the rectangular focal spot BF-indicated shaded-on its path from the initial position BF' to the final position BF" are directly adjacent to one another only at the inner edge of the incident area 22 without overlapping one another. Otherwise, there is a distance between the path sections 46a through 46h that becomes greater toward the outside edge of the incident area 22. In comparison to traditional x-ray tubes, however, a significantly greater part of the incident area 22 is swept by the focal spot BF before a previously swept path section of the incident area 22 is swept again after four revolutions of the rotating anode 16 (or 15 periods of the deflection signal $I_A$). Compared to a corresponding, traditional x-ray tube, a highly increased thermal loadability of the focal spot BF is thereby achieved. With the switch 45 open, certain overlaps of the radial path sections-one is indicated with shading in FIG. 2-swept when the focal spot moves from its final position BF" into its initial position BF' occur with the path sections 46a through 46h that are respectively swept when the focal spot BF moves from its initial position BF' into its final position BF". This does not, however, noticeably diminish the thermal loadability of the focal spot BF because of the slightness of the overlap.

Compared to the rotating anode of a corresponding, traditional x-ray tube, the rotating anode 16 according to FIG. 2 (which is provided with a large recess 47 at its underside) has a noticeably diminished mass. Taking the other parameters that influence the thermal radiation capability of the rotating anode 16 as well as the improved thermal loadability of the focal spot into consideration, the mass of the rotating anode 16 is selected such that a constant pre-temperature of the rotating anode 16 is achieved on the basis of an average temperature of 1200° C.

Figure 5A:
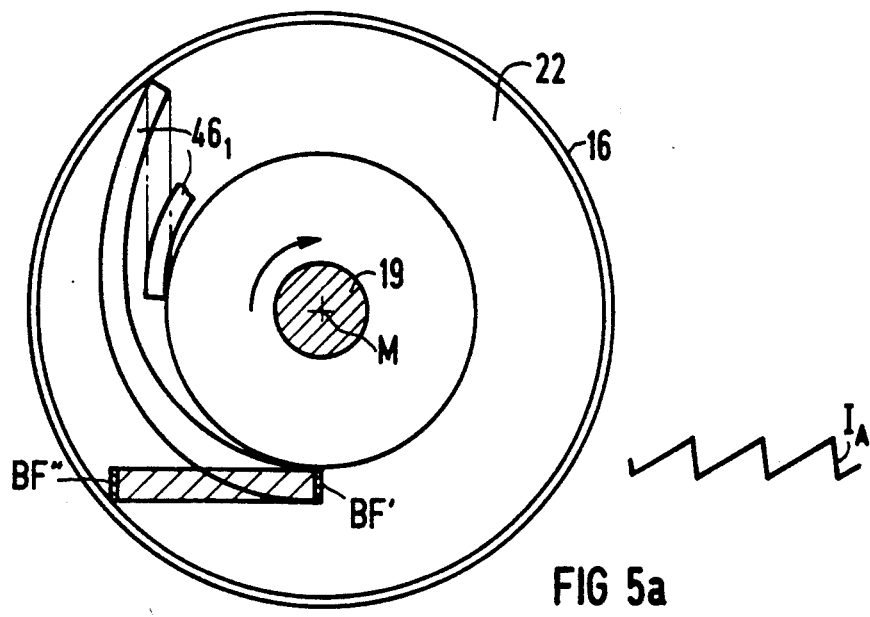
Figure 5B:
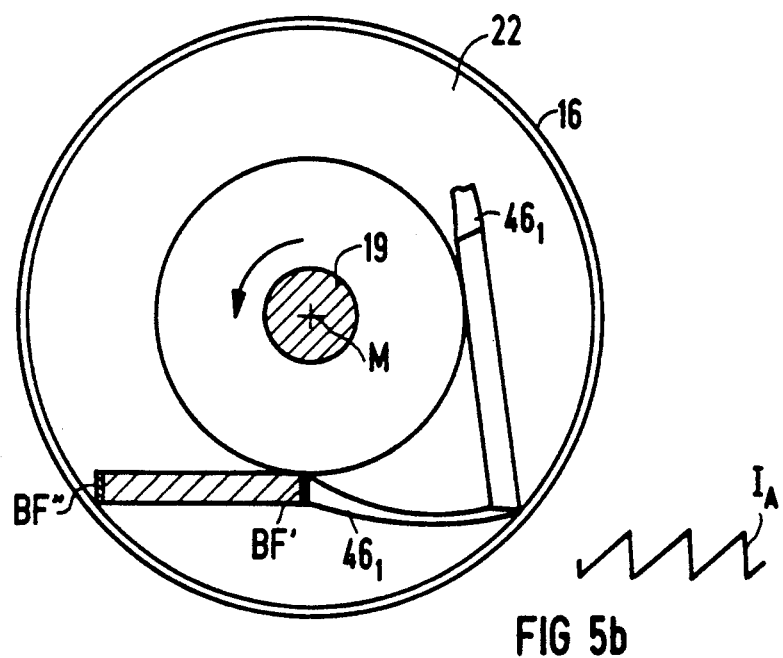

In an illustration analogous to FIG. 3, FIGS. 5a and 5c show the conditions when the focal spot is in fact displaced on a straight line path with an approximately sawtooth-shaped deflection signal 4, but on a path whose extension does not intersect the center axis M of the rotating anode 16. The movement of the focal spot from its initial position into its final position thereby ensues during the gradually rising, linear edge of the sawtooth-shaped deflection signal with a constant deflection speed with reference to the housing 17. In FIG. 5a, the rotation of the rotating anode ensues counter clockwise; in FIG. 5b, it ensues clockwise. On its path from the initial position into the final position on the incident area 22, the focal spot then respectively describes a path section having the shape of a section of a helix. As may be seen from FIG. 5a, wherein a path section $46_1$ is entered, the width thereof barely decreases toward the outside, whereas the width of the corresponding path section $46_1$ in FIG. 5b decreases greatly. In the case of FIG. 5a, moreover, a lengthening of the path sections $46_1$ compared to the conditions according to FIG. 3 occurs, and a shortening thereof occurs in the case of FIG. 5b. The lengthening or shortening of the path sections $46_1$ is maximal when the deflection motion of the focal spot BF ensues tangentially relative to the inner limitation of the incident area 22, as shown in FIGS. 5a and 5b. As shown in FIGS. 5a and 5b, the deflection motion preferably does not extend beyond the point at which the deflection motion comes into contact with the inner limitation of the incident area 22.

Figure 6:
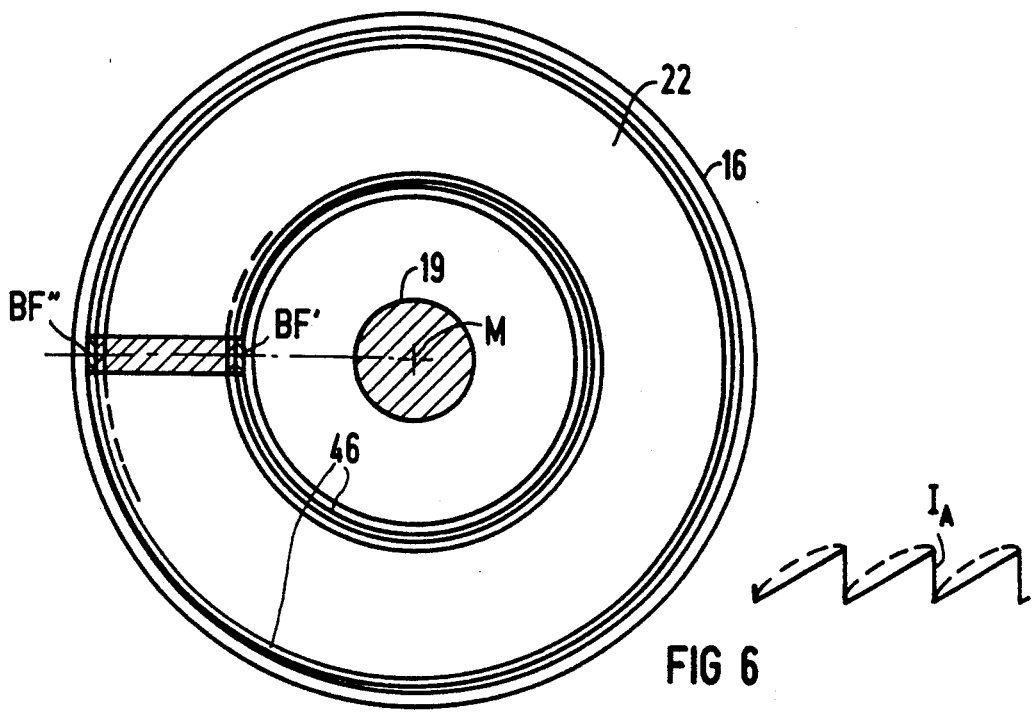
Figure 7:
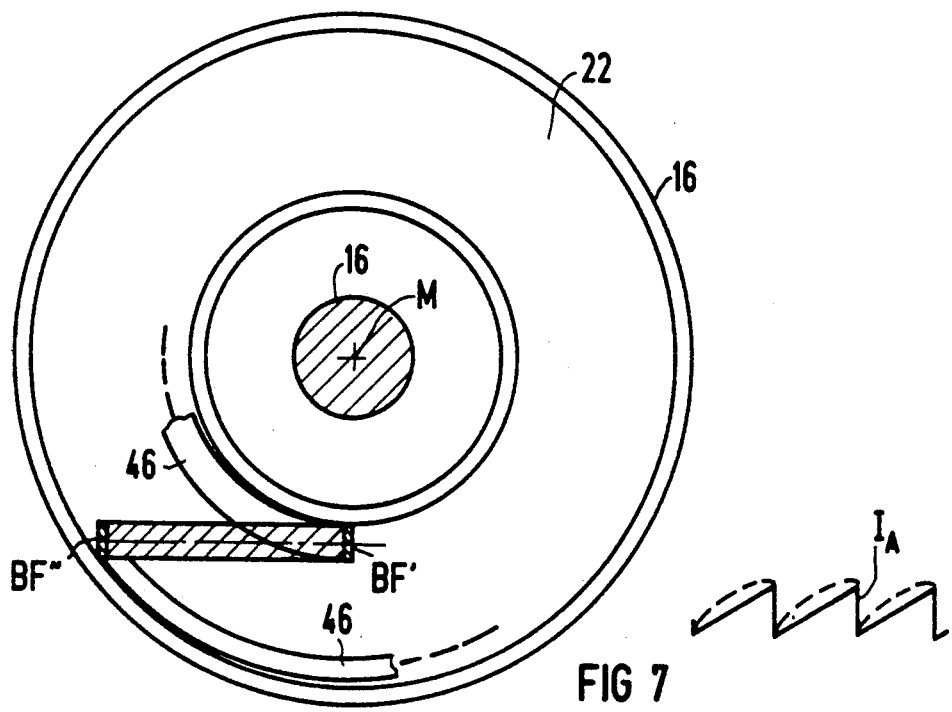

In an illustration analogous to FIGS. 3 and 5, FIG. 6 shows that path that the focal spot BF sweeps on the incident area 22 when the rotary frequency of the rotating anode 16 is multiply greater than the deflection frequency. This results in a helical path 46 between whose turns gradually increasing spacings toward the outside are present because of its gradually decreasing width toward the inside when a sawtooth-shaped deflection signal having a linearly rising edge is employed. These spacings become smaller with increasing length L of the focal spot BF compared to the width B thereof (L and B, see FIG. 4). These spacings can be entirely avoided if a deflection signal $I_A$ (indicated with broken lines in FIG. 6) is employed, in which case the deflection motion does not ensue with a constant speed but instead with a speed that gradually, slightly decreases toward the outside. Whereas FIG. 6 shows the conditions for the deflection of the focal spot BF on a straight-line path whose extension intersects the center axis M of the rotating anode 16, FIG. 7 shows the conditions for a straight-line path of the deflection motion whose extension does not intersect the center axis M. Here, too, the focal spot BF sweeps a helical path 46 on the incident area 22 whose width gradually increases toward the outside. Moreover, the spacing between the turns of the path 46 gradually increases toward the outside. The variation of the width of the path 46 and the variation of the spacing between the turns are greater for the conditions of FIG. 7 than for those of FIG. 6. These variations are maximum when the deflection motion is selected such that the focal spot BF is tangent to the inner edge of the incident area 22, as shown in FIG. 7. In the case of FIG. 7, as well, a deflection signal $I_A$ (indicated with broken lines in FIG. 7) must be employed that affects a faster deflection of the focal spot in the inner region of the incident area 22, when the turns of the helical path 46 are intended to be immediately adjacent to one another.

Figure 8:
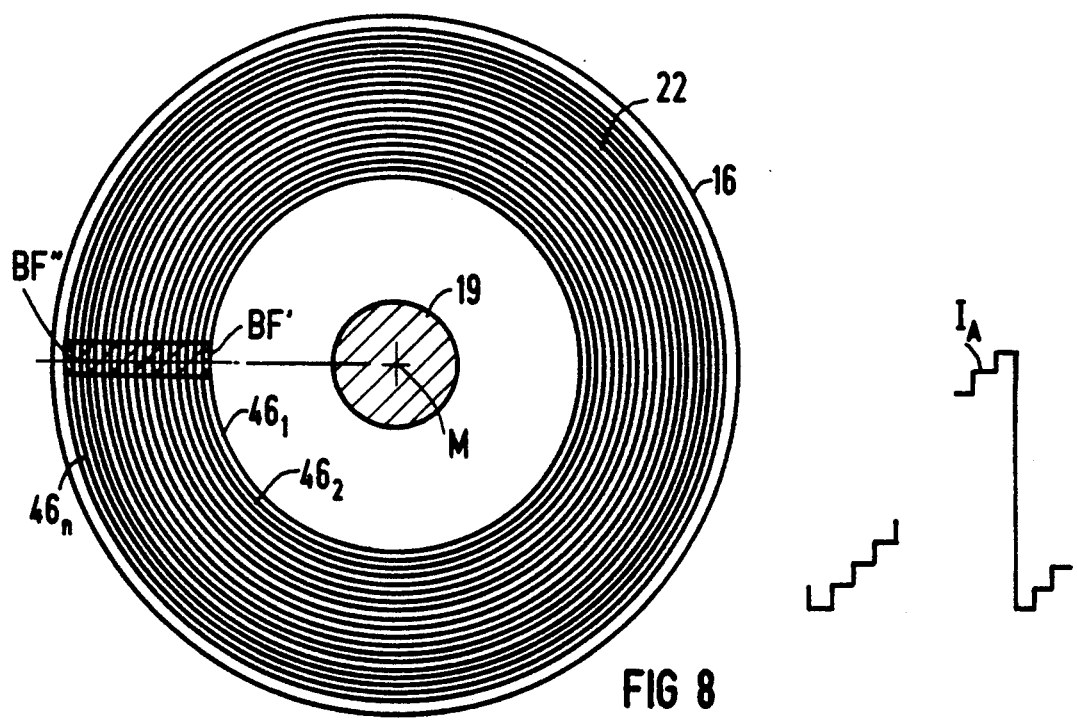
Figure 9:
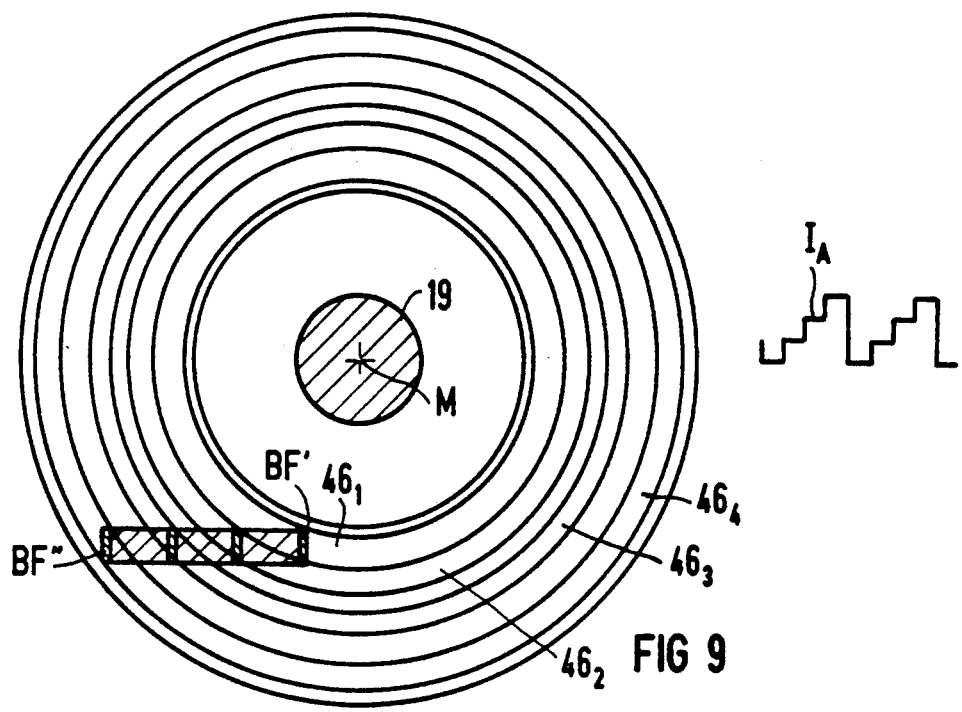

FIG. 8 shows the conditions that derive when the focal spot is in fact deflected on a straight-line path whose extension intersects the rotational axis M of the rotating anode 16, but is deflected with a deflection signal $I_A$ having a step-shaped curve according to FIG. 8, instead of a sawtooth deflection signal. The focal spot BF then discontinuously moves from the initial position BF' to the final position BF'' via a number of intermediate positions, whose number is dependent on the number of steps in the deflection signal $I_A$. The signal shape of the deflection signal $I_A$ is such that the focal spot dwells in the initial position BF', in every intermediate position and in the final position BF'' for the duration of an entire revolution of the rotating anode 16. Given a plurality of n−2 intermediate positions, the focal spot BF then sweeps an annular region $46_1$ through $46_n$ of the incident area 22 during each of n revolutions of the rotating anode 16. If a deflection of the focal spot BF by the same amount ensues for each step of the step-shaped deflection signal $I_A$, spacings that gradually increase toward the outside occur between the paths $46_1$ through $46_n$, since the paths $46_1$ through $46_n$ become gradually narrower toward the outside. Only the two innermost paths $46_1$ and $46_2$ can be immediately adjacent to one another. If all paths $46_1$ through $46_j$ are desired to be immediately adjacent with one another, a deflection signal $I_A$ must be employed that effects a gradually decreasing deflection of the focal spot toward the outside per step in a suitable way. In FIG. 8, the paths $46_1$ through $46_n$ are shown of equal width and immediately adjacent to one another for simplicity. The conditions for a step-shaped deflection signal $I_A$ and for the deflection of the focal spot BF along a straight-line path that does not intersect the middle axis M of the rotating anode are shown in FIG. 9 for a deflection signal $I_A$ having three steps. Accordingly, the deflection of the focal spot from the initial position BF' to the final position BF'' ensues via two intermediate positions. FIG. 9 very clearly shows the outwardly decreasing width of the annular paths $46_1$ through $46_4$ as well as the outwardly increasing spacings between these paths. The changes in width and spacing are again maximum if the path along which the focal spot BF is deflected proceeds tangentially vis-a-vis the inner limitation of the incident area 22. The conditions illustrated in FIG. 9 are valid for a deflection signal $I_A$ that effects a deflection of the focal spot BF of the same size per step. If a suitable, different stepshaped deflection signal $I_A$ is employed that effects and outwardly decreasing deflection of the focal spot per step, not only will the two innermost annular paths swept by the focal spot (as shown) be immediately adjacent, but all annular paths swept by the focal spot will be immediately adjacent to one another. This permits a greater plurality of annular paths on the incident area 22 at the same time under certain circumstances.

It must be pointed out that the employment of deflection signals that lead to a variable speed of the focal spot BF with reference to the housing 17 on its path from the initial position BF' to the final position BF'' can cause problems in the CT measuring process (particularly in the data compilation).

Figure 10:
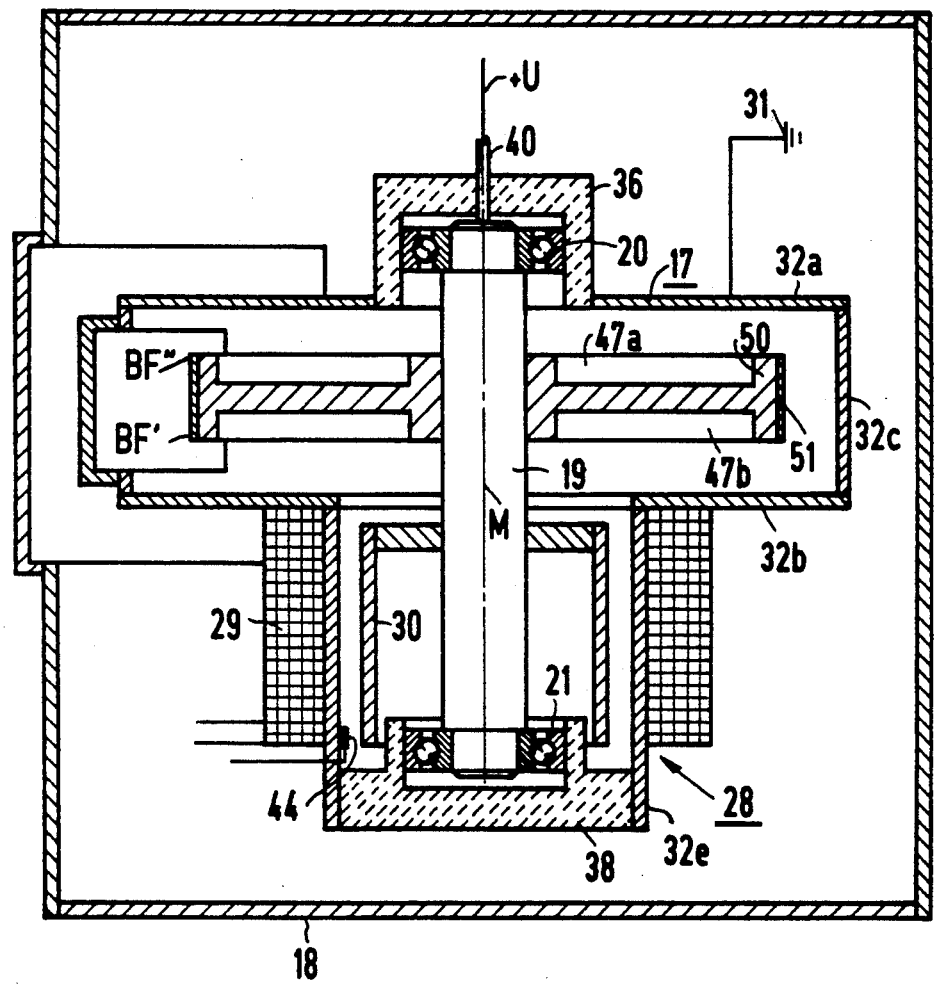
FIG. 10 is a schematic illustration of a longitudinal section through a further embodiment of an x-ray tube constructed in accordance with the principles of the present invention.
Figure 11:
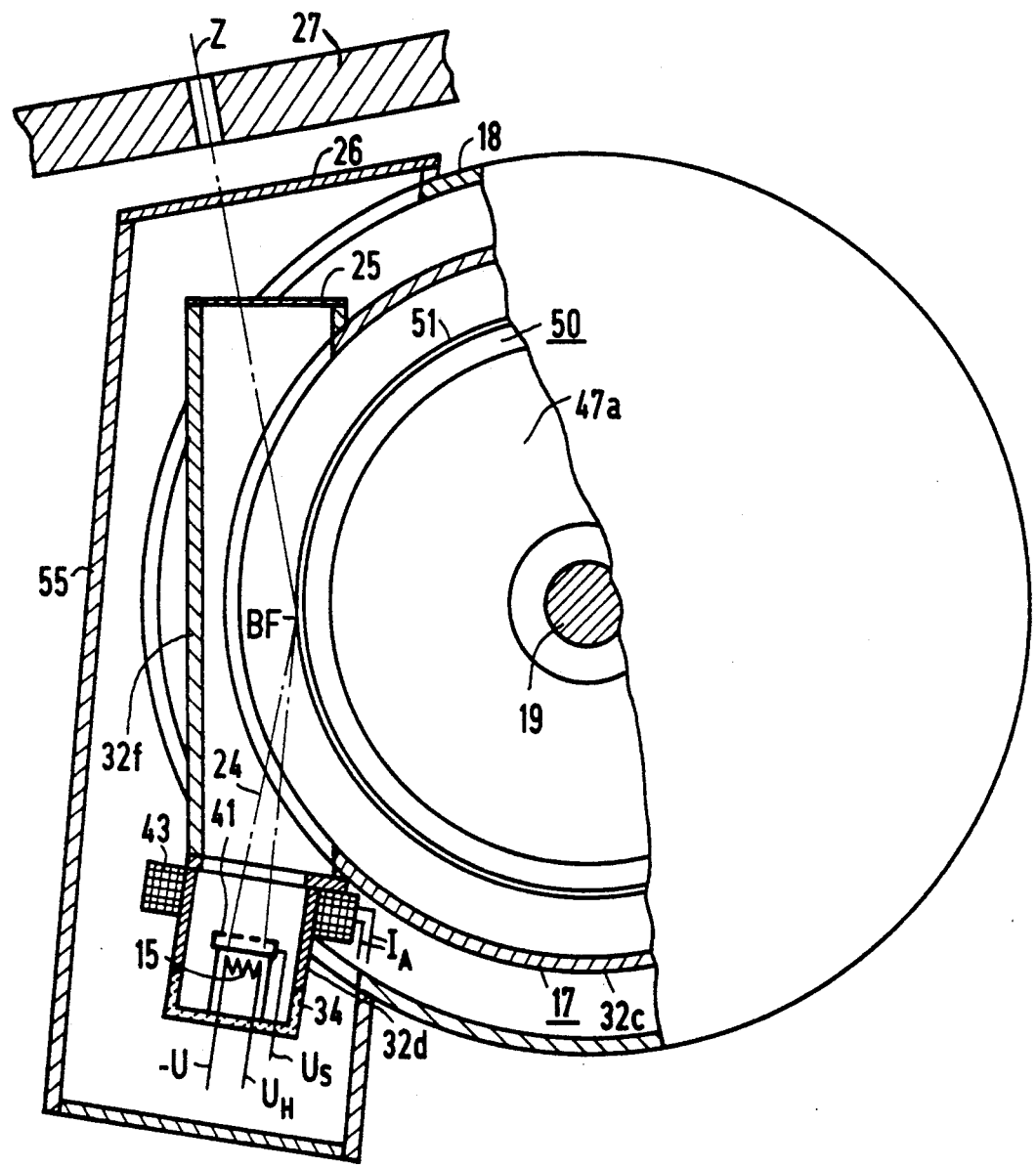
FIG. 11 is an end view of the x-ray tube of FIG. 10 in a partially cut away view.

FIGS. 10 and 11 show a further exemplary embodiment of the invention which is consistent in terms of critical points with that set forth above, for which reason the same or similar parts are provided with the same reference characters. The major difference compared to the embodiments set forth above is that a rotating anode 50 having an incident area 51 shaped as a cylindrical envelope is provided, and the cathode 15 together with the housing part 32d and the insulator 34 are attached to a tubular housing part 32f attached approximately tangentially to the housing part 32c. The housing part 32f has a rectangular cross section. The protective housing 18 is provided with a protective housing part 55 that corresponds to the housing part 32f. The beam exit window 25 is arranged at a continuation of the housing part 32f. The beam exit window 26 of the protective housing is arranged at a continuation of a part 25 of the protective housing 18 that corresponds to the housing part 37f. The cathode 15 is arranged such that the electron beam 24 impinges the incident area 51. The deflection of the electron beam 24 with the deflection coil 43 to which the deflection signal $I_A$ is supplied, ensues such that the focal spot BF moves between an initial position BF' and a final position BF'' parallel to the middle axis M. A slope of the middle axis M of the shaft 19 with reference to the plane of the drawing of FIG. 10 is not provided. The rotating anode 50 is provided with two recesses 47a and 47b that serve the same purpose as the recess 47.

Figure 12:
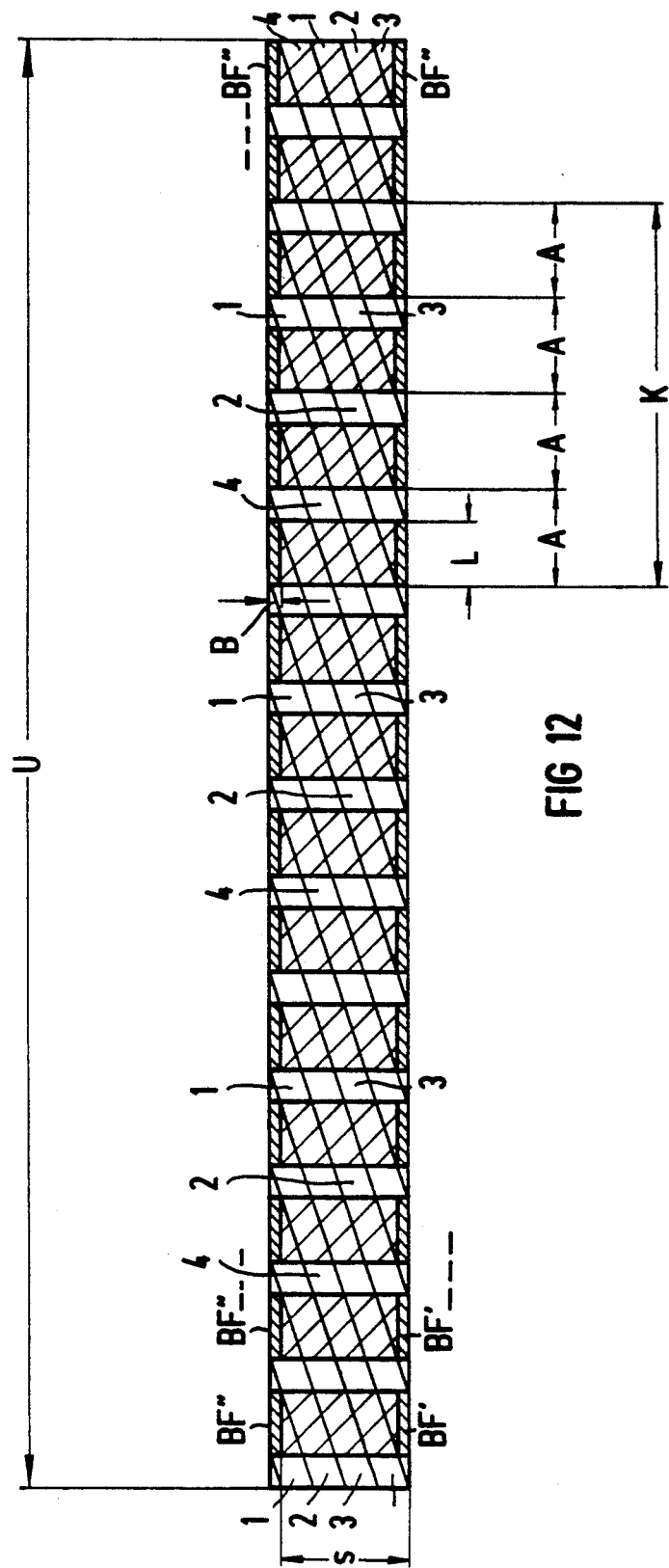
FIGS. 12 through 16 are highly schematic illustrations of view of the incident area of the rotating anode of the x-ray tube of FIG. 10 for different deflection signals $I_A$.

FIG. 12 shows the developed view of the incident area 51. FIG. 12 thereby shows that path 52 that the focal spot BF sweeps on the incident area 51 when it is periodically moved from its initial position BF' into its final position BF'' with a constant speed with reference to the housing 17 and in a negligibly short time from its final position BF'' into its initial position BF'. As in the case of FIG. 3, the rotating anode 50 has a rotatory frequency that amounts to 4/15 of the deflection frequency. Fifteen complete periods of the deflection signal $I_A$ thus occur during four revolutions of the rotating anode 50 during its motion from the initial position BF' to the final position BF''. The focal spot BF thereby describes a series of helical line-shaped path sections on the incident area 51, that appear as slanting path sections in the developed view of FIG. 11. Since the deflection frequency $f_A$ is selected according to the equations $$f_A = (U/p)(1-p)f_D$$

or $$f_A = ((mB)/S(1-mL/U))f_D$$

the path sections respectively swept on the incident area 51 by the focal spot BF on its path from the initial position BF' to the final position BF'' are directly adjacent to one another without overlapping one another, as shown in FIG. 12. With the exception of small, triangular regions in the developed view at the start and at the end of each path section, the entire incident area 52 is thereby swept by the focal spot, whereby a previously swept region of the incident area 51 is only swept again after four complete revolutions of the rotating anode.

In the indicated equations, U stands for the circumference of the incident area 51. So that no overlaps of the path sections swept by the focal spot BF on its path from the initial position BF' to the final position BF'' arise, and so that these are immediately adjacent to one another, $$m = U/A$$

and $$p = K/A$$

must be valid, with p and m being positive, whole numbers. The quantity A is the width-measured in circumferential direction-of the path sections swept by the focal spot BF on its path from the initial position BF' to the final position BF'' (see FIG. 12). The quantity K is that dimension by which the rotating anode 50 continues to turn during a period of the deflection signal $I_A$ (see FIG. 12). The quantity s is the deflection path of the focal spot BF; B is the width and L is the length of the focal spot BF (see FIG. 12); $f_D$ is the rotatory frequency of the rotating anode 50. In FIG. 12, m has the value 15 whereas p has the value 4.

Figure 13:
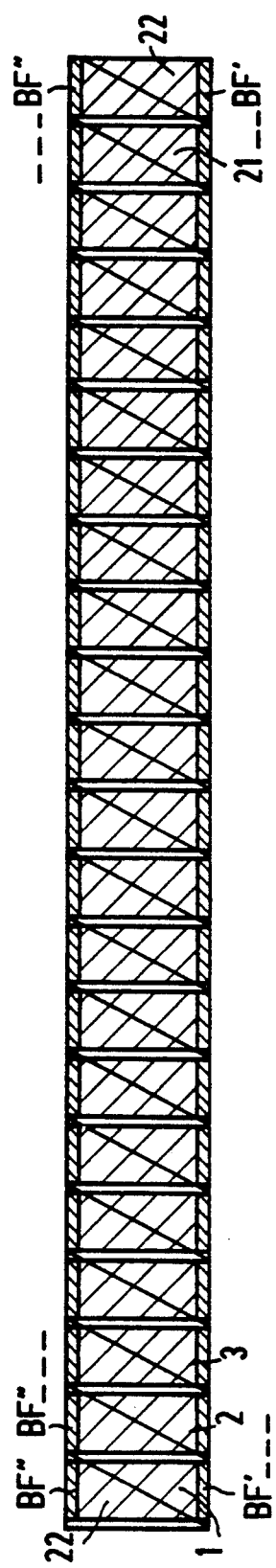
Figure 14:
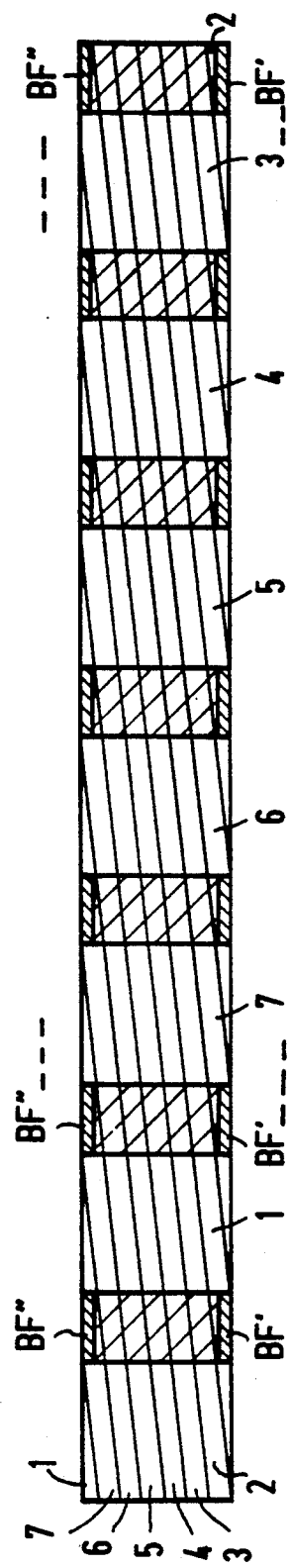
Figure 15:
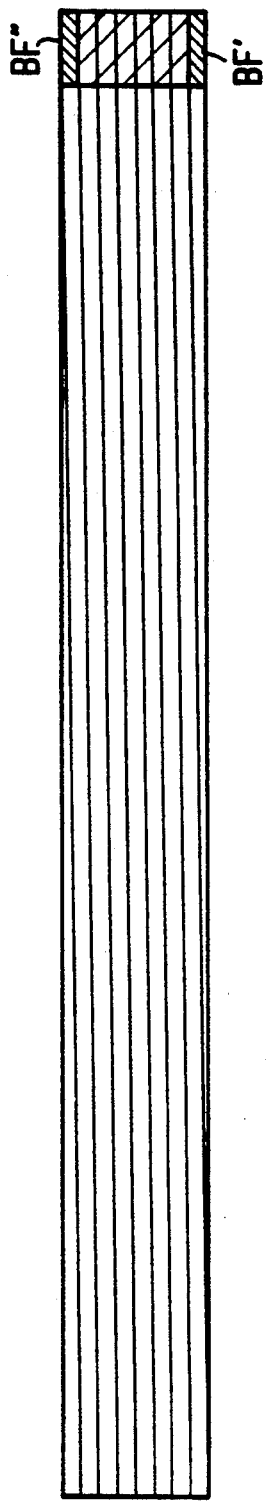

FIGS. 13 through 15 show the conditions for various limit values of p. FIG. 13 shows the conditions that are present when p assumes the value 1. In this case, the rotating anode 50 continues to turn during a period of the deflection signal $I_A$ by a dimension that corresponds to the width-measured in circumferential direction-of the path sections swept by the focal spot on its path from the initial position BF' into the final position BF''. The maximally possible frequency of the deflection signal $I_A$ without overlap of the path sections swept by the focal spot on its path from the initial position BF' to the final position BF'' thus occurs. Also valid for the conditions illustrated in FIG. 3, moreover, is m=22. FIG. 14 shows the conditions for p=m−1. In this case, a deflection frequency derives such that the rotating anode 50 turns during a period of the deflection signal $I_A$ exactly by a dimension that corresponds to the circumference of the incident area 51 diminished by the width-measured in circumferential direction of the incident area 51-of the path sections swept by the focal spot BF on its path from the initial position BF' to the final position BF''. Moreover, m=7 and p=6 are valid in FIG. 14. FIG. 15 shows the conditions that derive for m=1. On its path from the initial position BF' to the final position BF'', the focal spot BF then sweeps a single, helical line-shaped path whose turns are directly adjacent to one another. The frequency of the deflection signal $I_A$ then has its minimum value. For the conditions shown in FIG. 15, p=7 applies.

Figure 16:
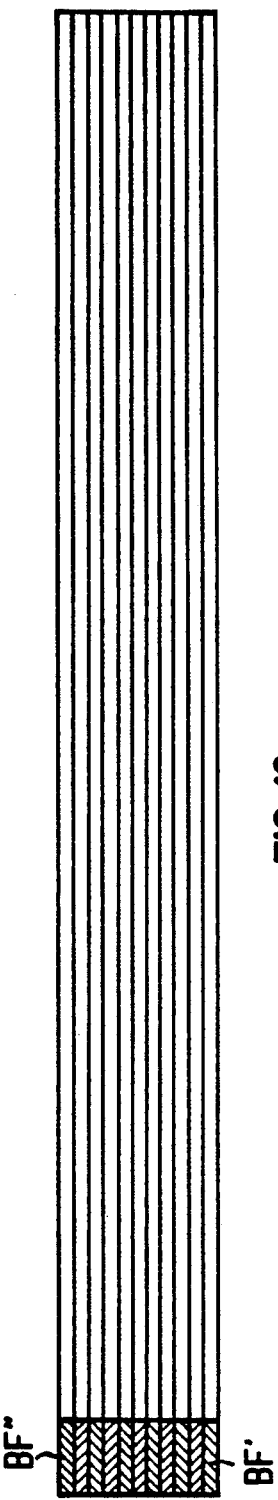

Whereas FIGS. 12 through 15 are based on a sawtooth-shaped deflection signal $I_A$ that deflects the focal spot BF with a constant speed, FIG. 16 shows the conditions that derive for a step-shaped deflection signal $I_A$ which effects a movement per step of the focal spot BF by a dimension corresponding to its width B and whereby the rotating anode 50 turns by a full revolution during the duration of one step. The focal spot BF then sweeps an annular path on the incident area 51 during every step of the deflection signal $I_A$, whereby the paths are immediately adjacent to one another without overlapping. The number of annular paths derives from the quotient s/B, and $$f_A = (B/S)f_D$$

is valid for the deflection frequency.

The above equations can be analogously applied to, for example, conical frustum-shaped or planar incident areas, whereby the conditions at the inner edge of the incident area should form the basis.

The regions of the incident area swept by the focal spot BF with respect to their shape, their relative area as well as the exploited portion of the overall incident area available are listed in Table 1 for a rotating anode having a planar annular incident area whose outside diameter amounts to 160 mm and whose inside diameter amounts to 60 mm and are also listed therein for a rotating anode having a cylindrical incident area with a diameter of 160 mm, for a rotatory frequency of the rotating anode $f_D$ of 50 Hz, a focal length L=9 mm and focal width B=0.9 mm as well as for a deflection signal $I_A$, whereby the time required for the motion of the focal spot BF from its final position BF'' back into its initial position BF' is negligibly short with reference to specific figures set forth above. How long a specific point of the incident area is charged (T1) by the electron beam during a revolution of the rotating anode, how long it lasts until a specific point of the incident area is again charged (T2) by the electron beam and the duration during which a point of the incident area is charged (T3) during one second by the electron beam are also recited for the individual cases. The times T1 through T3 are thereby recited in milliseconds.

It is clearer from Table 1 that x-ray tubes of the invention, particularly those having a cylindrical incident area, are substantially superior to x-ray tubes of the prior art in view of their thermal loadability.

The above-described exemplary embodiments are only to be understood by way of example with respect to the shape of the incident area, the signal shape of the deflection signal $I_A$ as well as with respect to the direction and the shape of the path along which the focal spot BF is deflected. In particular, there is the possibility of providing a second deflecting coil that deflects the electron beam 24 in a different direction than the deflecting coil 43. There is then the possibility of also displacing the focal spot BF along curved paths. Known electrostatic deflection means can also be employed for the electron beam 24 instead of electromagnetic deflection means in the form of one or more deflecting coils.

Figure 17:
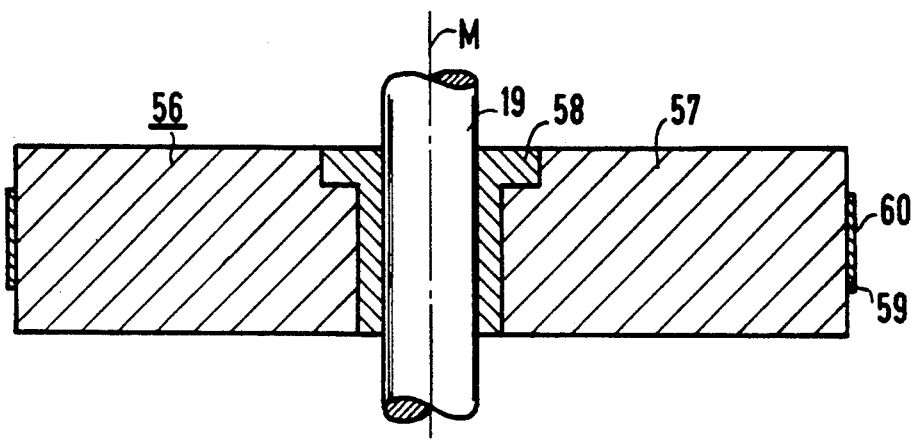
FIG. 17 is a sectional view of a modification of a rotating anode employable in an x-ray tube constructed in accordance with the principles of the present invention.

FIG. 17 shows a version of a rotating anode 56 that can be employed instead of the rotating anode 50 in the x-ray tube according to FIGS. 10 and 11. The rotating anode 56 has a solid base member 57 of graphite that is torsionally connected to the shaft 19 via a hub 58. The base member 57 has its cylindrical outer surface provided with a layer 59 of a tungsten-rhenium alloy, so that a cylindrical envelope-shaped incident area 60 is available. A heat emission that is additionally improved thereby derives as a consequence of employing graphite as the material for the base member 57.

The preferred employment of the x-ray tube of the invention is in computer tomography. Other employments, for example, in radiation therapy, are also possible.

Although modifications and changes may be suggested by those skilled in the art, it is the intention of the inventors to embody within the patent warranted hereon all changes and modifications as reasonably and properly come within the scope of their contribution to the art.

TABLE I

| Position and Length of the Deflection | Deflection Mode | Shape | Relative Area Content | Utilized Surface | $T_1$(ms) | $T_2$(ms) | $T_3$(ms) | Comments |
|---|---|---|---|---|---|---|---|---|
| in circum-ferential direction 2 mm | discontinuous | 1 annulus | 1 | 18% | 0.043 | 20 | 2.1 | prior art |
| tangentially relative to the inner edge of the incident area 50 mm | FIG. 9 | 4 separate annuluses | ca. 2.5 | <50% | 0.072 | 80 | 0.9 | outwardly increasing spacings between the path sections |
| | FIG. 7 | 1 helical path | ca. 2.5 | <50% | 0.072 | 80 | 0.9 | |
| | FIGS. 5a & 5b | paddlewheel-shaped | ca. 2 | <47% | >0.017 | 20 | >0.9 | due to equidistance of the path sections |
| radially 50 mm | FIG. 8 | approximately 50 separate annuluses | 4.6 | 86% | 0.96 | 1120 | 0.86 | no spacings between the path sections given |
| | FIG. 6 | 1 helical path | 4.5 | 84% | 0.96 | 1120 | 0.86 | optimum deflection signal outwardly decreasing spacings between the path sections |
| | FIGS. 3 & 4 | paddlewheel-shaped | 2.5 | 47% | >0.017 | 20 | >0.86 | |
| parallel to the center axis of the incident area 50 mm | FIG. 16 | 56 separate annuluses | 6.6 | 100% | 0.36 | 1120 | 0.32 | no spacings between the path sections |
| | FIG. 15 | 1 helical line-shaped path | 6.5 | 98% | 0.36 | 1120 | 0.32 | |
| | FIG. 14 | parallelogram-shaped paths in tight succession | 6.6 | 100% | 0.0064 | 20 | 0.32 | |

We claim as our invention:

1. An x-ray tube comprising:
an evacuated housing;
cathode means in said housing for generating an electron beam;
a rotary anode disposed in said housing and having an anode surface with an incident area on which said electron beam is incident on a focal spot to cause the generation of x-rays, said anode surface having a circumferential direction;
means for rotating said rotary anode at a rotary frequency;
deflection means for interacting with said electron beam for deflecting said electron beam; and
control means for operating said deflection means and said means for rotating so that said deflection means deflects said electron beam at a deflection frequency which is not a whole number multiple of said rotary frequency and said means for rotating rotates said rotary anode at a rotary frequency which is not a whole number multiple of said deflection frequency.

2. An x-ray tube as claimed in claim 1 wherein said control means is a means for operating said deflection means for deflecting said electron beam through a distance between said initial position and said final position, measured transversely relative to said circumferential direction, which is at least four times the extent of said focal spot measured transversely relative to said circumferential direction.

3. An x-ray tube as claimed in claim 1 wherein said control means is a means for operating said deflection means for deflecting said electron beam through a distance between said initial position and said final position, measured transversely relative to said circumferential direction, which is at least twenty-five times the extent of said focal spot measured transversely relative to said circumferential direction.

4. An x-ray tube as claimed in claim 1 wherein said control means is a means for operating said deflection means for deflecting said electron beam through a distance between said initial position and said final position, measured transversely relative to said circumferential direction, which is substantially equal to the extent of said focal spot measured transversely relative to said circumferential direction.

5. An x-ray tube as claimed in claim 1 wherein said incident area has a cylindrical envelope shape.

6. An x-ray tube as claimed in claim 1 wherein said control means includes means for generating a saw tooth deflection signal supplied to said deflection means for deflecting said electron beam.

7. An x-ray tube as claimed in claim 1 wherein said control means includes means for generating a step-shaped deflection signal supplied to said deflection means for deflecting said electron beam.

8. An x-ray tube as claimed in claim 1 wherein said rotating anode has a rotary frequency and wherein said control means operates said deflection means for deflecting said electron beam at a deflection frequency, and further comprising means for fixedly coupling said deflection frequency and said rotary frequency.

9. An x-ray tube as claimed in claim 1 wherein said incident area has dimensions and a geometrical shape, and wherein said control means includes means for generating a deflection signal supplied to said deflection means for deflecting said electron beam in a deflection motion having a deflection path along said deflection direction, said means for generating said deflection signal generating said deflection signal dependent on said deflection direction and path, said rotary frequency, said dimensions and geometrical shape of said incident area, a distance traversed by said focal spot between said final position and said initial position measured transversely relative to said circumferential direction, and the extent of said focal spot in said circumferential direction and in a direction transversely relative to said circumferential direction, for causing said focal spot to successively sweep respective regions of said incident area as said focal spot moves from said initial position to said final position which are disposed in maximally close proximity to each other without overlapping.

10. An x-ray tube as claimed in claim 9 wherein said means for generating said deflection signal is a means for generating said deflection signal so that said regions swept by said focal spot are immediately adjacent to each other.

11. An x-ray tube as claimed in claim 1 wherein said control means includes means for generating a deflection signal supplied to said deflection means for deflecting said electron beam, said deflection signal having a signal shape for causing said focal spot to move from said initial position to said final position along a straight line.

12. An x-ray tube as claimed in claim 1 wherein said control means includes means for generating a deflection signal supplied to said deflection means for deflecting said electron beam, said deflection signal having a signal shape for causing said focal spot to move discontinuously from said initial position to said final position through at least one intermediate position.

13. An x-ray tube as claimed in claim 12 wherein said means for generating said deflection signal generates said deflection signal with a signal shape for causing said focal spot to remain in said initial position and in each intermediate position and in said final position for the duration of a complete revolution of said rotating anode.

14. An x-ray tube as claimed in claim 1 wherein said control means includes means for generating a deflection signal supplied to said deflection means for deflecting said electron beam, said deflection signal having a signal shape for causing said focal spot to move from said initial position to said final position in a continuous deflection motion.

15. An x-ray tube as claimed in claim 14 wherein said control means is a means for operating said deflection means for deflecting said electron beam for causing said focal spot to move with a constant speed with reference to said evacuated housing between said initial position and said final position.

16. An x-ray tube as claimed in claim 1 wherein said control means includes means for operating said deflection means for deflecting said electron beam to cause said focal spot to return to said initial position after attaining said final position.

17. An x-ray tube as claimed in claim 16 further comprising means for suppressing the generation of said x-rays in the time between said focal spot attaining said final position and said focal spot being returned to said initial position.

18. An x-ray tube as claimed in claim 16 wherein said control means is a means for operating said deflection means for deflecting said electron beam to move said focal spot from said initial position to said final position in a time which is equal to the time between said focal spot attaining said final position and being returned to said initial position.

19. An x-ray tube as claimed in claim 16 wherein said control means is a means for operating said deflection means for deflecting said electron beam to move said focal spot from said initial position to said final position in a time which is a multiple longer than the time between said focal spot attaining said final position and being returned to said initial position.

20. An x-ray tube as claimed in claim 1 wherein said anode has a mass and said anode surface has a size selected for establishing a stationary pre-temperature of said rotating anode given continuous operation of said x-ray tube with maximum power.

21. An x-ray tube as claimed in claim 1 wherein said incident area is planar and has an annular shape.

22. A method for operating an x-ray tube in a computer tomography system comprising the steps of:
in an x-ray tube, generating an electron beam and directing said electron beam to a rotating anode having an anode surface with an incident area on which said electron beam is incident on a focal spot to cause the generation of x-rays, said anode surface having a circumferential direction;
directing said x-rays onto a radiation detector with an examination subject disposed between said x-ray tube and said radiation detector and generating output signals from said detector corresponding to the radiation incident on said detector;
moving said x-ray tube and said radiation detector through a plurality of successive scanning positions relative to said examination subject;
sampling said output signals in said plurality of successive scanning positions; and
periodically radially deflecting said electron beam in a deflection direction intersecting said circumferential direction for moving said focal spot radially on said anode surface from an initial position to a final position once per scanning position.

23. A method as claimed in claim 22 wherein the step of deflecting said electron beam is further defined by generating a saw tooth deflection signal for deflecting said electron beam.

24. A method as claimed in claim 22 wherein the step of deflecting said electron beam is further defined by generating a step-shaped deflection signal for deflecting said electron beam.

25. A method as claimed in claim 22 comprising the additional step of selecting a mass for said anode and a size for said anode surface for establishing a stationary pre-temperature of said rotating anode given continuous operation of said x-ray tube with maximum power.

26. A method as claimed in claim 22 the step of deflecting said electron beam is further defined by wherein deflecting said electron beam through a distance between said initial position and said final position, measured transversely relative to said circumferential direction, which is at least four times the extent of said focal spot measured transversely relative to said circumferential direction.

27. A method as claimed in claim 22 wherein the step of deflecting said electron beam is further defined by said control means is a means for operating said deflection means for deflecting said electron beam through a distance between said initial position and said final position, measured transversely relative to said circumferential direction, which is at least twenty-five times the extent of said focal spot measured transversely relative to said circumferential direction.

28. A method tube as claimed in claim 22 wherein the step of deflecting said electron beam is further defined by deflecting said electron beam through a distance between said initial position and said final position, measured transversely relative to said circumferential direction, which is substantially equal to the extent of said focal spot measured transversely relative to said circumferential direction.

29. A method as claimed in claim 22 wherein said rotating anode has a rotary frequency and wherein said electron beam is deflected at a deflection frequency, and comprising the addition step of selecting said rotary frequency, and comprising the addition step of selecting said rotary frequency and said deflection frequency such that said rotary frequency is not a whole number multiple of said deflection frequency and said deflection frequency is not a whole number multiple of said rotary frequency.

30. A method as claimed in claim 29 wherein the step of deflecting said electron beam is further defined by deflecting said electron beam at a deflection frequency which is higher than said rotary frequency.

31. A method as claimed in claim 29 wherein the step of deflecting said electron beam is further defined by deflecting said electron beam at a deflection frequency which is lower than said rotary frequency.

32. A method as claimed in claim 22 wherein said rotating anode has a rotary frequency and wherein said electron beam is deflected at a deflection frequency, and comprising the additional step of fixedly coupling said deflection frequency and said rotary frequency.

33. A method as claimed in claim 22 wherein said rotating anode has a rotary frequency, wherein said incident area has dimensions and a geometrical shape, and wherein said electron beam is deflected in a deflection motion having a deflection path along said deflection direction, and wherein the step of deflecting said electron beam is further defined by deflecting said electron beam dependent on said deflection direction and path, said rotary frequency, said dimensions and geometrical shape of said incident area, a distance traversed by said focal spot between said final position and said initial position measured transversely relative to said circumferential direction, and the extent of said focal spot in said circumferential direction and in a direction transversely relative to said circumferential direction, for causing said focal spot to successively sweep respective regions of said incident area as said focal spot moves from said initial position to said final position which are disposed in maximally close proximity to each other without overlapping.

34. A method as claimed in claim 33 wherein the step of deflecting said electron beam so that said regions swept by said focal spot are immediately adjacent to each other.

35. A method as claimed in claim 22 wherein the step of deflecting said electron beam is further defined by generating a deflection signal for deflecting said electron beam having a signal shape for causing said focal spot to move from said initial position to said final position along a straight line.

36. A method as claimed in claim 22 wherein the step of deflecting said electron beam is further defined by generating a deflection signal for deflecting said electron beam having a signal shape for causing said focal spot to move discontinuously from said initial position to said final position through at least one intermediate position.

37. A method as claimed in claim 36 wherein the step of generating said deflection signal is further defined by generating said deflection signal with a signal shape for causing said focal spot to remain in said initial position and in each intermediate position and in said final position for the duration of a complete revolution of said rotating anode.

38. A method as claimed in claim 22, wherein the step of deflecting said electron beam is further defined by generating a deflection signal for deflecting said electron beam having a signal shape for causing said focal spot to move from said initial position to said final position in a continuous deflection motion.

39. A method as claimed in claim 38 wherein said rotating anode is disposed in an evacuated housing and wherein the step of deflecting said electron beam is further defined by deflecting said electron beam for causing said focal spot to move with a constant speed with reference to said evacuated housing between said initial position and said final position.

40. A method as claimed in claim 22 wherein the step of deflecting said electron beam is further defined by deflecting said electron beam to cause said focal spot to return to said initial position after attaining said final position.

41. A method as claimed in claim 40 comprising the additional step of suppressing the generation of said x-rays in the time between said focal spot attaining said final position and said focal spot being returned to said initial position.

42. A method as claimed in claim 40 wherein the step of deflecting said electron beam is further defined by deflecting said electron beam to move said focal spot from said initial position to said final position in a time which is equal to the time between said focal spot attaining said final position and being returned to said initial position.

43. A method as claimed in claim 40 wherein the step of deflecting said electron beam is further defined by deflecting said electron beam to move said focal spot from said initial position to said final position in a time which is a multiple longer than the time between said focal spot attaining said final position and being returned to said initial position.

44. An x-ray tube comprising:
an evacuated housing:
cathode means in said housing for generating an electron beam;
a rotary anode disposed in said housing and having an anode surface with an incident area on which said electron beam is incident on a focal spot to cause the generation of x-rays, said anode surface having a circumferential direction and said incident area having dimensions and a geometrical shape;
means for rotating said rotary anode at a rotary frequency;

deflection means for interacting with said electron beam for deflecting said electron beam; and control means for operating said deflection means for generating a deflection signal supplied to said deflection means for deflecting said electron beam in a deflection motion having a deflection path along said deflection direction, said means for generating said deflection signal generating said deflection signal dependent on said deflection direction and path, said rotary frequency, said dimensions and geometrical shape of said incident area, a distance traversed by said focal spot between said final position and said initial position measured transversely relative to said circumferential direction, and the extent of said focal spot in said circumferential direction and in a direction transversely relative to said circumferential direction, for causing said focal spot to successively sweep respective regions of said incident area as said focal spot moves from said initial position to said final position which are disposed in maximally close proximity to each other without overlapping.

45. An x-ray tube as claimed in claim 44 wherein said control means is a means for operating said deflection means for deflecting said electron beam at a deflection frequency selected such that said rotary frequency is not a whole number multiple of said deflection frequency and said deflection frequency is not a whole number multiple of said rotary frequency.

46. An x-ray tube as claimed in claim 1 wherein said control means is a means for operating said deflection means for deflecting said electron beam at a deflection frequency which is higher than said rotary frequency.

47. An x-ray tube as claimed in claim 1 wherein said control means is a means for operating said deflection means for deflecting said electron beam at a deflection frequency which is lower than said rotary frequency.

48. An x-ray tube as claimed in claim 44 wherein said control means is a means for operating said deflection means for deflecting said electron beam through a distance between said initial position and said final position, measured transversely relative to said circumferential direction, which is at least four times the extent of said focal spot measured transversely relative to said circumferential direction.

49. An x-ray tube as claimed in claim 44 wherein said control means is a means for operating said deflection means for deflecting said electron beam through a distance between said initial position and said final position, measured transversely relative to said circumferential direction, which is at least twenty-five times the extent of said focal spot measured transversely relative to said circumferential direction.

50. An x-ray tube as claimed in claim 44 wherein said control means is a means for operating said deflection means for deflecting said electron beam through a distance between said initial position and said final position, measured transversely relative to said circumferential direction, which is substantially equal to the extent of said focal spot measured transversely relative to said circumferential direction.

51. An x-ray tube as claimed in claim 44 wherein said control means is a means for operating said deflection means for deflecting said electron beam at a deflection frequency which is higher than said rotary frequency.

52. An x-ray tube as claimed in claim 44 wherein said control means is a means for operating said deflection means for deflecting said electron beam at a deflection frequency which is lower than said rotary frequency.

53. An x-ray tube as claimed in claim 44 wherein said rotating anode has a rotary frequency and wherein said control means operates said deflection means for deflecting said electron beam at a deflection frequency, and further comprising means for fixedly coupling said deflection frequency and said rotary frequency.

54. An x-ray tube as claimed in claim 44 wherein said means for generating said deflection signal is a means for generating said deflection signal so that said regions swept by said focal spot are immediately adjacent to each other.

55. An x-ray tube as claimed in claim 44 wherein said control means includes means for generating a deflection signal supplied to said deflection means for deflecting said electron beam, said deflection signal having a signal shape for causing said focal spot to move from said initial position to said final position along a straight line.

56. An x-ray tube as claimed in claim 44 wherein said control means includes means for generating a deflection signal supplied to said deflection means for deflecting said electron beam, said deflection signal having a signal shape for causing said focal spot to move discontinuously from said initial position to said final position through at least one intermediate position.

57. An x-ray tube as claimed in claim 56 wherein said means for generating said deflection signal generates said deflection signal with a signal shape for causing said focal spot to remain in said initial position and in each intermediate position and in said final position for the duration of a complete revolution of said rotating anode.

58. An x-ray tube as claimed in claim 44 wherein said control means includes means for generating a deflection signal supplied to said deflection means for deflecting said electron beam, said deflection signal having a signal shape for causing said focal spot to move from said initial position to said final position in a continuous deflection motion.

59. An x-ray tube as claimed in claim 58 wherein said control means is a means for operating said deflection means for deflecting said electron beam for causing said focal spot to move with a constant speed with reference to said evacuated housing between said initial position and said final position.

60. An x-ray tube as claimed in claim 44 wherein said control means includes means for operating said deflection means for deflecting said electron beam to cause said focal spot to return to said initial position after attaining said final position.

61. An x-ray tube as claimed in claim 60 further comprising means for suppressing the generation of said x-rays in the time between said focal spot attaining said final position and said focal spot being returned to said initial position.

62. An x-ray tube as claimed in claim 60 wherein said control means is a means for operating said deflection means for deflecting said electron beam to move said focal spot from said initial position to said final position in a time which is equal to the time between said focal spot attaining said final position and being returned to said initial position.

63. An x-ray tube as claimed in claim 60 wherein said control means is a means for operating said deflection means for deflecting said electron beam to move said focal spot from said initial position to said final position in a time which is multiple longer than the time between said focal spot attaining said final position and being returned to said initial position.

64. An x-ray tube as claimed in claim 44 wherein said anode surface has a mass and size selected for establishing a stationary pre-temperature of said rotating anode given continuous operation of said x-ray tube with maximum power.

65. An x-ray tube as claimed in claim 44 wherein said incident area is planar and has an annular shape.

66. An x-ray tube as claimed in claim 44 wherein said incident area has a cylindrical envelope shape.

67. An x-ray tube as claimed in claim 44 wherein said control means includes means for generating a saw tooth deflection signal supplied to said deflection means for deflecting said electron beam.

68. An x-ray tube as claimed in claim 44 wherein said control means includes means for generating a step-shaped deflection signal supplied to said deflection means for deflecting said electron beam.

* * * * *